(12) United States Patent
Scheiderer et al.

(10) Patent No.: US 9,116,078 B1
(45) Date of Patent: Aug. 25, 2015

(54) SOIL SAMPLER AND METHOD

(71) Applicants: David Scheiderer, Milford Center, OH (US); Michel Grand, Irwin, OH (US); Dwayne Maddox, London, OH (US)

(72) Inventors: David Scheiderer, Milford Center, OH (US); Michel Grand, Irwin, OH (US); Dwayne Maddox, London, OH (US)

(73) Assignee: Integrated Ag Services, LTD, Milford Center, OH (US)

( * ) Notice: Subject to any disclaimer, the term of this patent is extended or adjusted under 35 U.S.C. 154(b) by 452 days.

(21) Appl. No.: 13/686,014

(22) Filed: Nov. 27, 2012

(51) Int. Cl.
*G01N 1/04* (2006.01)

(52) U.S. Cl.
CPC ........................ *G01N 1/04* (2013.01)

(58) Field of Classification Search
CPC .................................. G01N 1/12; G01N 1/04
See application file for complete search history.

(56) References Cited

U.S. PATENT DOCUMENTS

| | | | | |
|---|---|---|---|---|
| 3,625,296 | A * | 12/1971 | Mabry et al. | 173/24 |
| 4,304,139 | A * | 12/1981 | Johnson | 73/864.32 |
| 4,356,734 | A * | 11/1982 | Ivancsics | 73/864.31 |
| 4,869,115 | A * | 9/1989 | Edwards et al. | 73/864.31 |
| 5,394,949 | A | 3/1995 | Wright | |
| 5,435,399 | A * | 7/1995 | Peterson et al. | 175/20 |
| 5,741,983 | A * | 4/1998 | Skotnikov et al. | 73/864.45 |
| 6,016,713 | A | 1/2000 | Hale | |
| 6,044,324 | A | 3/2000 | Boerhave | |
| 6,119,531 | A * | 9/2000 | Wendte et al. | 73/863.52 |
| 7,216,555 | B2 * | 5/2007 | Drummond et al. | 73/864.45 |
| 7,255,016 | B2 * | 8/2007 | Burton | 73/864.45 |
| 7,552,654 | B2 | 6/2009 | Burton | |
| 8,286,857 | B2 | 10/2012 | Covely | |
| 8,613,234 | B1 * | 12/2013 | Harrell | 73/864.41 |
| 2005/0172733 | A1 * | 8/2005 | Drummond et al. | 73/864.41 |
| 2014/0095074 | A1 | 4/2014 | Covely | |
| 2014/0251032 | A1 * | 9/2014 | Scheiderer et al. | 73/864.43 |

* cited by examiner

*Primary Examiner* — John Fitzgerald
(74) *Attorney, Agent, or Firm* — Mark A. Navarre (57) ABSTRACT

An automatic soil sampler for taking samples of topsoil has a soil breakdown assembly that cuts a shallow furrow in the soil and moves debris to the side. Soil is collected with a sampling knife having a series of empty chambers adapted to receive samples of topsoil. A rotating discus is disposed opposite the soil sampling empty chambers for urging soil into the soil sampling empty chambers. A cup carrousel carries empty identified cups for receiving soil samples. A delivery assembly places one of the empty identified cup in a cup receiving station. A filling assembly connects the knife chambers carrying collected soil samples with the cup receiving station. The cups are filled with soil samples in a collecting station. Each filled cup has its identifier sent to memory along with the location at which the sample was taken.

7 Claims, 14 Drawing Sheets

SOIL SAMPLER AND METHOD

CROSS-REFERENCE TO RELATED APPLICATIONS

None.

STATEMENT REGARDING FEDERALLY SPONSORED RESEARCH

Not applicable.

BACKGROUND

This disclosure generally relates to soil sample collection and analysis, and more particularly to a soil sampler that can be operated manually or automatically.

Soil samples (usually the top 7 inches or so of the topsoil) are taken from farm fields and sent to a soil analysis lab to analyze the different soil nutrients contained in the sample. This analysis is used to determine the correct amount of nutrients to apply to farm fields. In the past, the process of collecting the soil sample was a slow tedious job done by using a hand probe. Recently some automation has been added to soil sampler equipment to remove some of the handwork, but none have significantly increased the speed of sampling. The disclosed system removes the hand labor, plus sampling time has been greatly decreased.

As an agronomist specializing in soil fertility I have noticed there is considerable variation of nutrient content as samples are taken across farm fields. The only way to be able to accurately measure this variability is to increase the number of samples being taken within a field. With the disclosed auto sampler the time required to collect the samples has been greatly reduced. We can now collect many more samples per field per hour, therefore greatly improving our ability to accurately measure the variability without increasing our labor to collect the samples. With accurate nutrient maps our customers need only apply nutrients where needed, reducing environmental risk and improving their profitability.

BRIEF SUMMARY

The driver of a small utility tractor operates the disclosed auto sampler. The operator manages the system from the cab. The task of the auto sampler is to cycle a collection knife into the soil for approximately 5 seconds collecting a soil sample; it then raises the knife out of the soil and through a series of motions places the collected soil into a marked storage container. When the sampler cycles the knife into the ground it marks the GPS location and tags the storage container identification number in a data file. Once the auto sampler has traveled a determined distance (usually 150') away from the previous point it automatically starts the sampling task again. It repeats this task each time the auto sampler has traveled the determined distance (example: 150'). It does this repeatedly throughout the field. As the auto sampler continues to collect samples across the field, it places the samples in a storage tray until the field is completed.

Thus, disclosed is an automatic soil sampler for taking samples of topsoil that has a soil breakdown assembly that cuts a shallow furrow in the soil and moves debris to the side. Soil is collected with a sampling knife having a series of chambers adapted to receive samples of topsoil. A rotating discus is disposed opposite the soil sampling empty chambers for urging soil into the soil sampling empty chambers. A cup carrousel carries empty identified cups for receiving soil samples. A delivery assembly places one of the empty identified cups in a cup receiving station. A filling assembly connects the knife chambers carrying collected soil samples with the cup receiving station. The cups are filled with soil samples and moved into a collection station. Each filled cup has its identifier sent to memory along with the location at which the sample was taken.

BRIEF DESCRIPTION OF THE DRAWINGS

For a fuller understanding of the nature and advantages of the present media and process, reference should be had to the following detailed description taken in connection with the accompanying drawings, in which.

DETAILED DESCRIPTION

Figure 1:
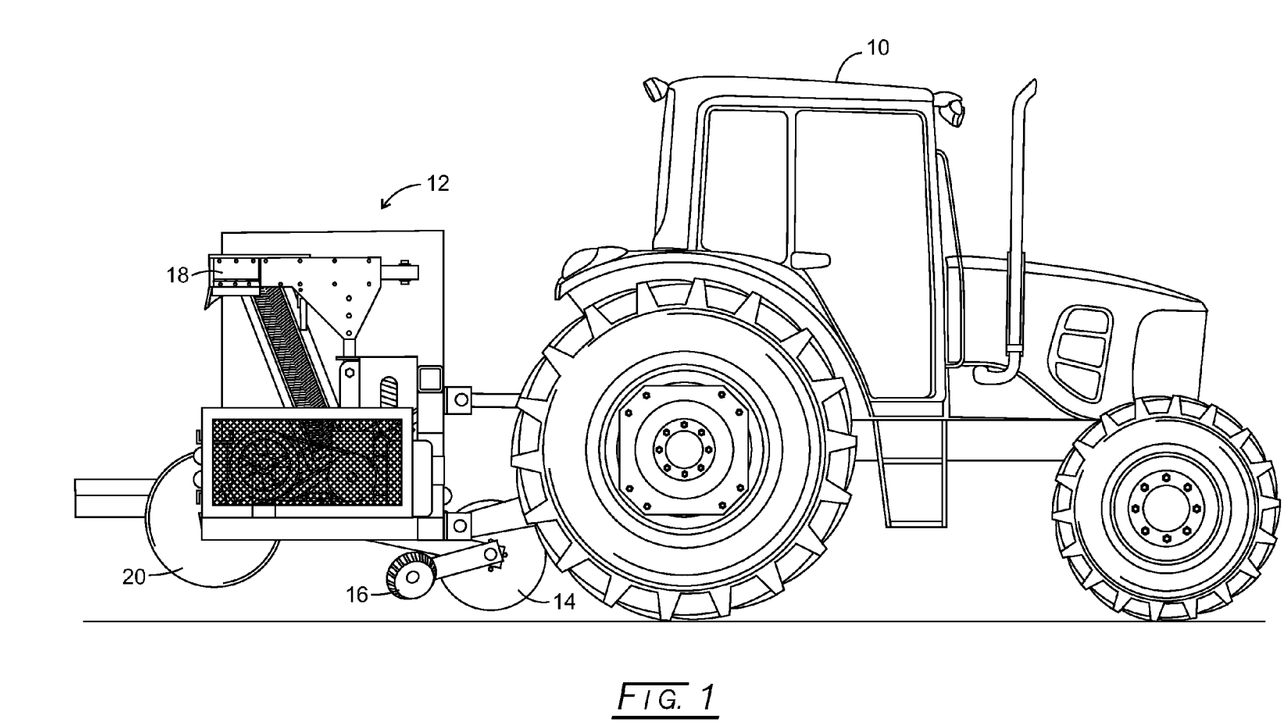
FIG. 1 is a side view of a tractor with the disclosed soil sampler mounted at its rear in a home position.
Figure 2:
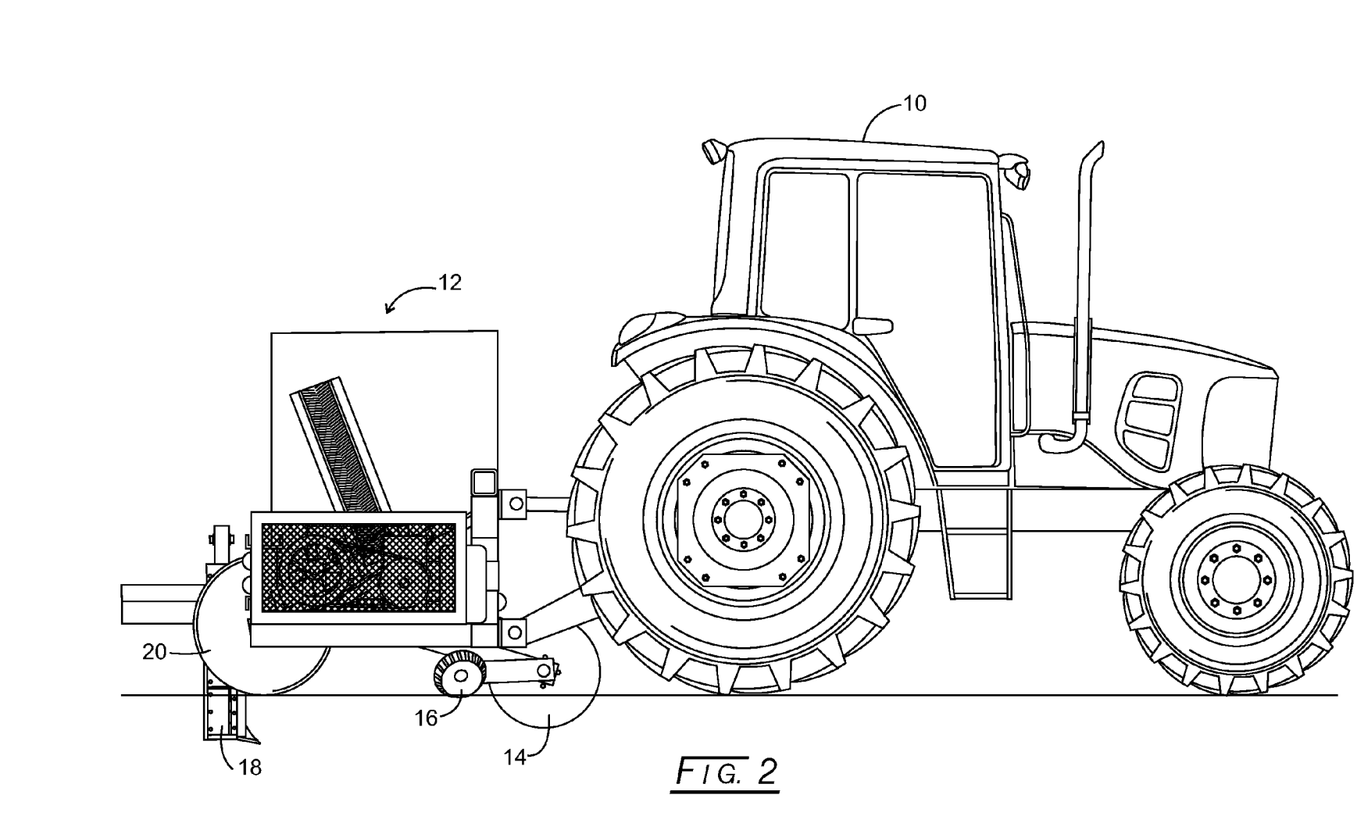
FIG. 2 is a side view like that in FIG. 2, but with the soil sampler in its active, soil sampling position.

Referring initially to FIGS. 1 and 2, a tractor, 10, has the disclosed soil sampler, 12, mounted at its rear. All electrical and hydraulic power for soil sampler 12 is provided from tractor 10. The only requirement for such mounting is that soil sampler 12 can be lowered from its home position shown in FIG. 1 to its soil sampling or active position shown in FIG. 2 and vice versa. Such lowering and raising of farm implements is common for a tractor to implement.

Soil sampler 12 has a large rotating disk, 14, that cuts a furrow into the soil to be sampled. A set for inwardly toed teethed disks, 16, clear a path by shoving rocks and debris aside so that relatively clean soil is confronted by a collection knife assembly, 18, that actually takes the soil samples. A canted wheel, 20, pushes soil towards the collection knife assembly in order for soil samples to be taken.

Figure 3:
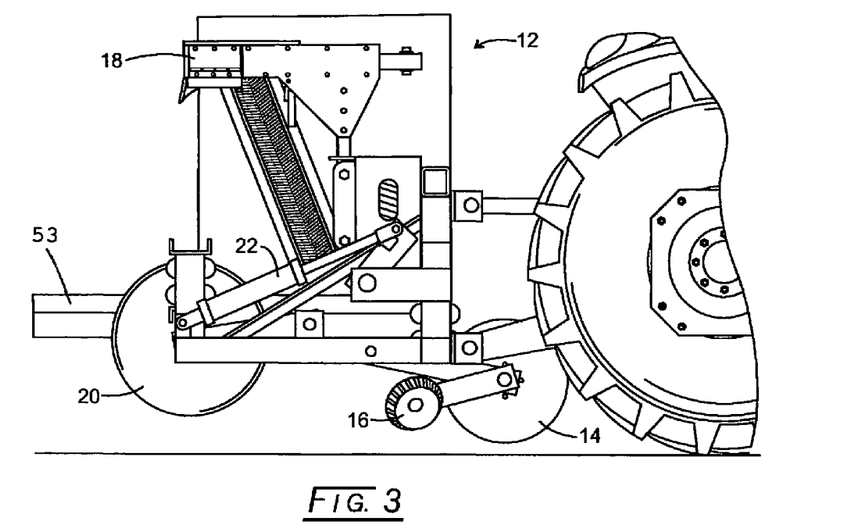
FIG. 3 is a close up view of the soil sampler with the protective covering removed to reveal the inside of the soil sampler in its home position.
Figure 4:
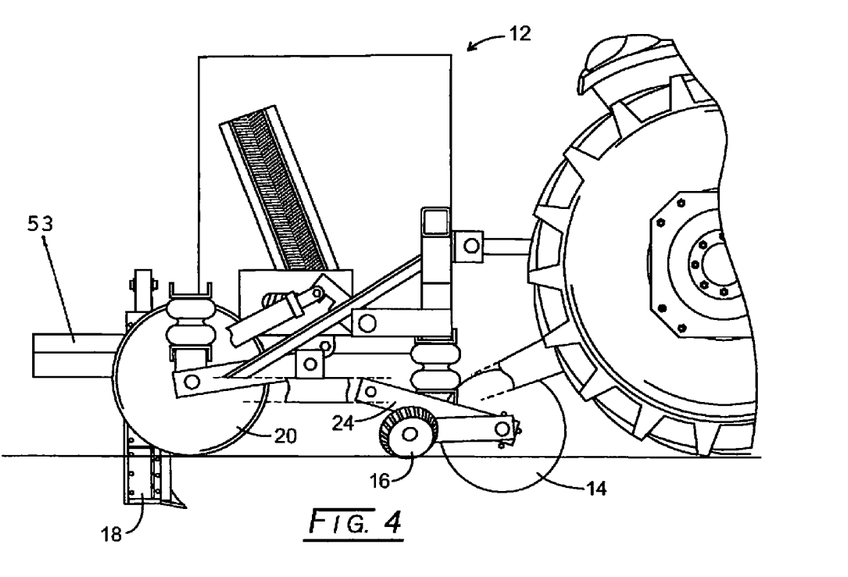
FIG. 4 is a close up view of the soil sample like that in FIG. 3, but with the soil sampler in it active soil sampling position.

Referring now to FIG. 3, all components are in their home position away from the ground. A cylinder assembly, 22, raises and lowers collection knife assembly 18. Rotating disk 14 and toed disks 16, as a combined assembly, are held in place by a pivoting arm, 24. When arm 24 is released, the combined assembly of rotating disk 14 and toed disks 16 are forced into the ground by a down force air bag in an operating condition.

Figure 5:
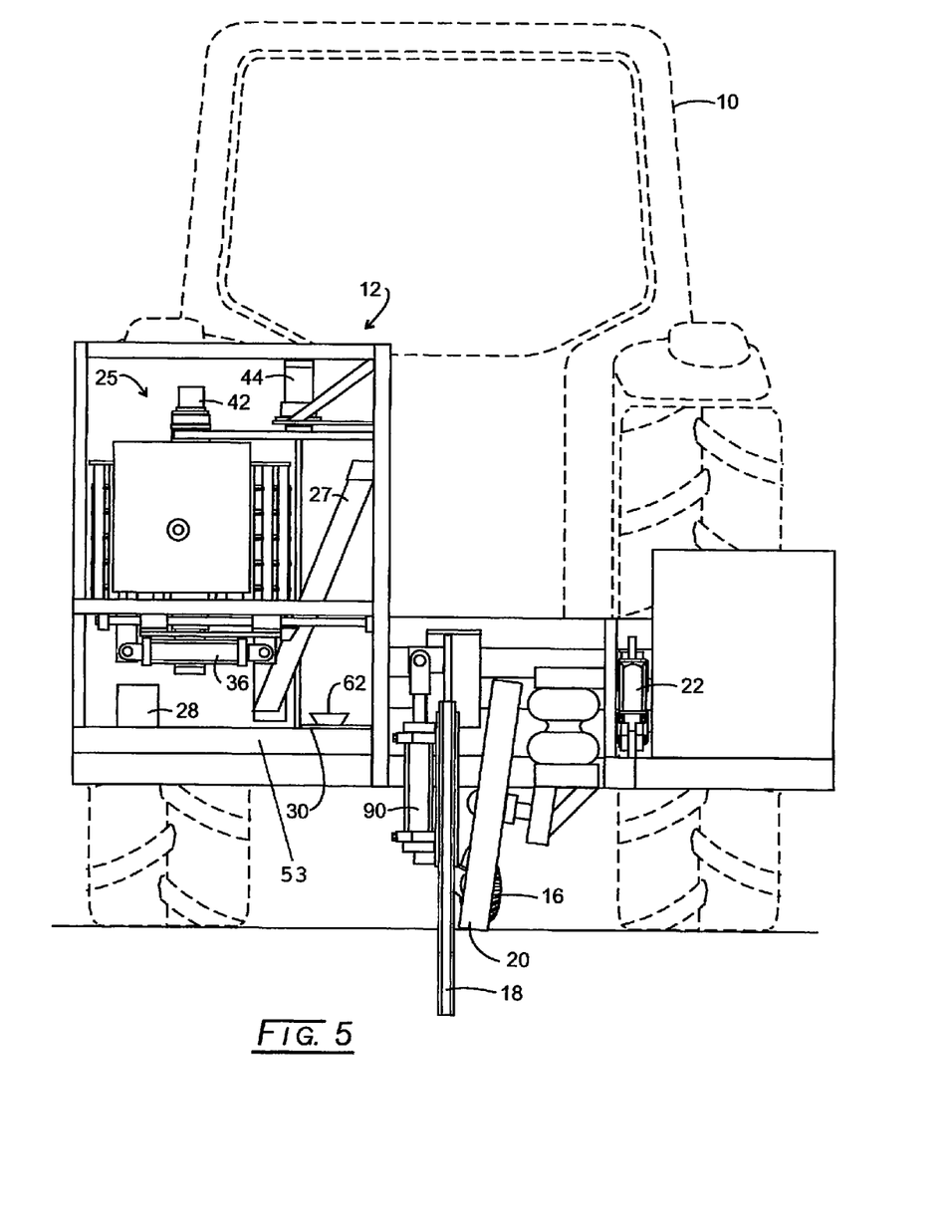
FIG. 5 is a rear view of the soil sampler in its active soil sampling position showing the wheel soil furrowing assembly.

FIG. 5 is a rear view of soil sampler 12 shown in FIG. 2. Canted wheel 16 is seen in position to push soil towards collection knife assembly 18 so that such soil can be collected therewithin. Inwardly toed disks 16 can bee seen in this view also. Carrousel cup assembly, 25, is seen in this view also with all outer metal protective box removed. It will be described in detail below, as will the soil transfer system that transfers soil from collection knife assembly 18 to a cup dispensed from carrousel cup assembly 25. A cylinder assembly, 22, raises and lowers collection knife assembly 18.

Figure 6:
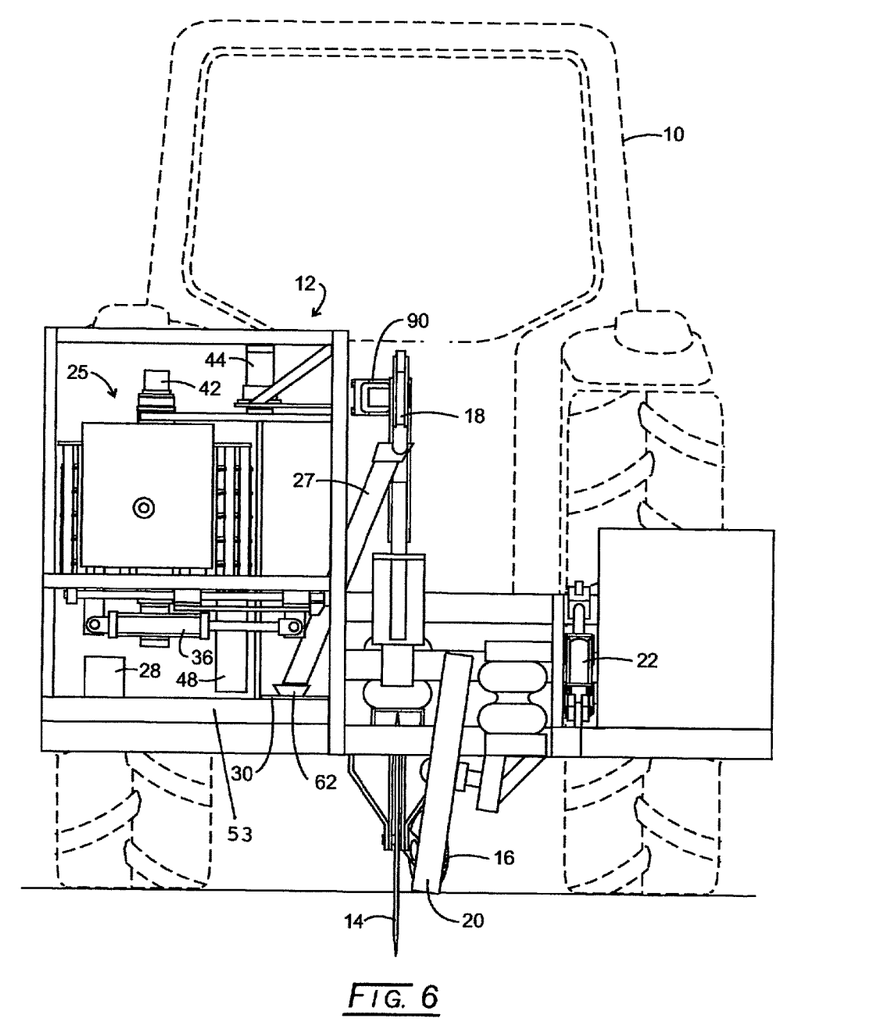
FIG. 6 is a rear view of the soil sampler in its active soil sampling position showing the knife soil collection assembly.

In FIG. 6, collection knife assembly 18 has been raised, while rotating disk 14, towed disks 16, and canted wheel 20 remain in their downward, operating position. They will be retracted upwardly subsequently.

Figure 7:
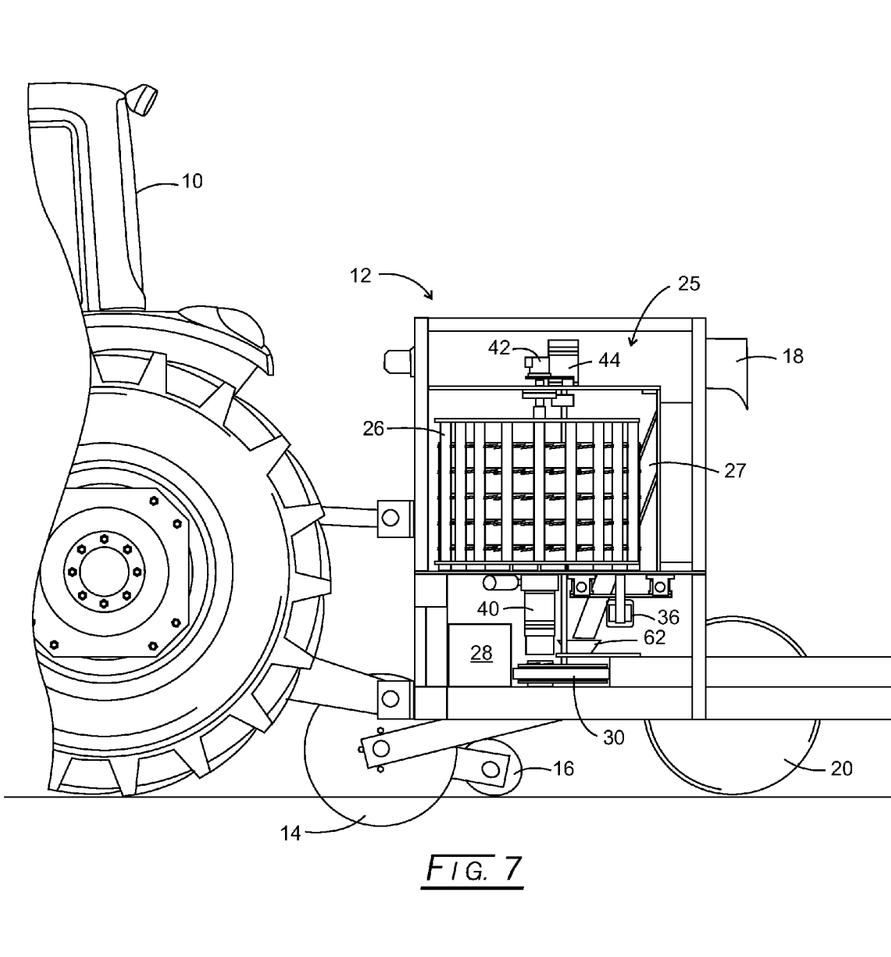
FIG. 7 is close up side view of the opposite side of the soil sampler with outer covering removed to show the cup carrousel assembly.

Hydraulic controls, 28, also are shown in FIGS. 5, 6, and 7. A cup carousel motor, 40, rotates cups in cup carousel 26 into position using an encoder 42 for proper placement, for transfer to cup mover 30. A hydraulic motor, 44, rotates cup mover 30, with the position of cup mover, 30, determined by an associated encoder, 46. Cup carousel 26 contains, say, 200 cups with the bottom cups resting on a table, 47. Each time a new cup is needed for a collected soil sample, cup carousel 26 rotates 18° so that a cup aligns with a hole formed in table 47 and below which is an alignment tube, 48, through which the bottom most cup rests on the slide gate, 49, which opens and drops the cup through the alignment tube, 48, into the cup mover assembly 30, such as a cup, 50.

Figure 15:
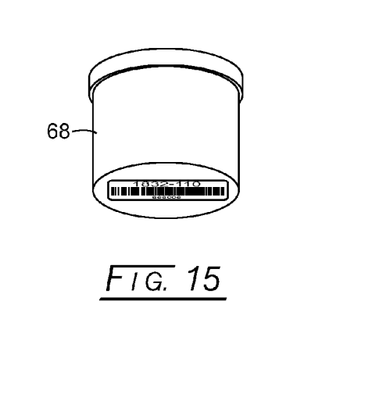
FIG. 15 is an isometric view of a collection cup revealing the bar code on its bottom surface.

A second floor, 52, retains cup mover assembly 30. Below cup 50 is an opening formed in floor 52 and through which a bar code reader, 54, reads a bar code, 56, that is disposed on the outside bottom floor of cup 50, as illustrated in FIG. 15. Cup assembly 68 in FIG. 15 also is shown with a lid, 58, that can be put on each cup once tractor 10 returns home from a farm field.

An air nozzle, 61, disposed to the side of cup 50, that is in position to rotate to receive a soil sample, blows away any loose dirt so that such loose dirt does not foul up any of the moving components. An air nozzle, 60, blows air across bar code reader 54 to clean it off. Other nozzles, some disposed horizontally, could be supplied, nozzles, 60 and 61 being representative of such compressed air nozzles only.

Returning now to the soil sample transfer process, soil housed within the collection chambers in collection knife assembly 18 is urged into transfer tube 27 and then through a funnel, 62, whose bottom spout empties into collection cup 50. Again, compressed air through a nozzle, 91 is provided to clean up any loose dirt in the area of the disclosed soil sample collection system. Hydraulic cylinder assembly moves collection chamber within the knife assembly 18 back and forth, for example, twice to urge the collected soil sample into transfer tube 27. As the soil samples are being transferred into transfer tube 27, compressed air through a nozzle, 91, is applied to clean out any remaining lodged soil in the collection chambers in collection knife assembly 18.

Soil housed with in collection knife assembly 18 is transferred to transfer tube 27 in which soil falls under the influence of gravity and compressed air into a collection cup, such as a cup, 50, (see FIG. 8) that is seated upon cup mover assembly 30. A cylinder assembly, 36, moves the transfer tube 27 from a home position, such as is depicted in FIG. 5 during soil collection, into a soil transfer position, such as is depicted in FIG. 6, during which soil is transferred into a soil cup for later analysis. It should be pointed out that the tractor onboard GPS position is noted during soil collection and then associated with a bar code that each cup has and which will be described below. In the manual mode with an operator seated in seat assembly 14, manually actuates the start procedure to initiate the automated steps necessary for soil samples to be taken.

Referring now to FIG. 5, soil sampler 12 is shown in its active or soil sampling mode, a canted wheel 20 can be seen in a position to urge or push soil towards to the entry of the collection chambers housed in collection knife assembly 18. Inwardly toed disks 16 that clear a path by shoving rocks and debris aside also are revealed in FIG. 3. A soil capture slot, 85, is located to one side of collection knife assembly 18. The adjustable slot, 83, sheers a thin sliver of soil as the soil passes the knife assembly when in the soil. This sheering action forces the soil sample to flow into the soil collection chamber, 72-76, as the collection knife assembly, 18, slices through the soil profile. Once the collection knife assembly is raised, 18, cleanout guard opens, 84, the transfer tube, 27, extends, transferring the soil to the waiting cup, 50, located in the cup mover, 30.

Figure 8:
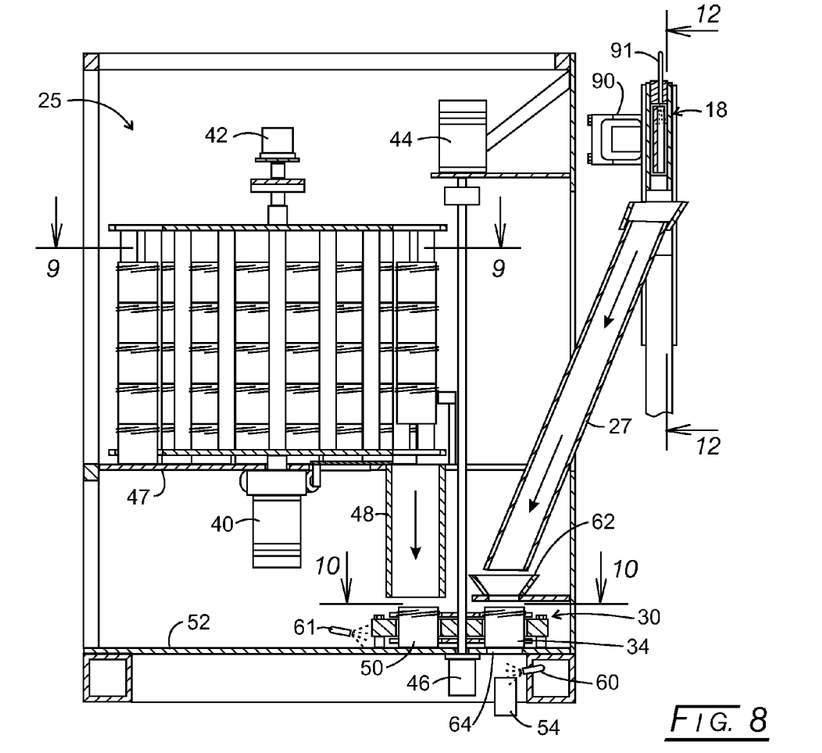
FIG. 8 is a rear view of the soil sampler with outer covering removed to reveal the soil collection system and cup carrousel assembly.
Figure 9:
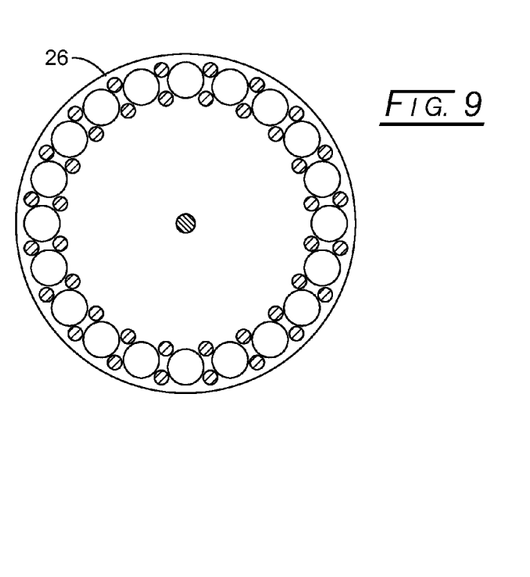
FIG. 9 is a sectional view taken along line 9-9 of FIG. 8.
Figure 10:
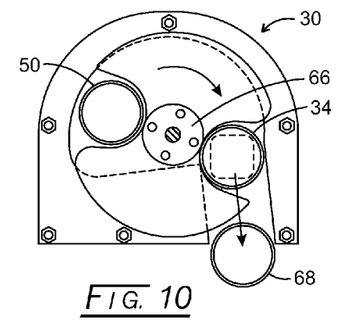
FIG. 10 is a sectional view taken along line 10-10 of FIG. 8.
Figure 11:
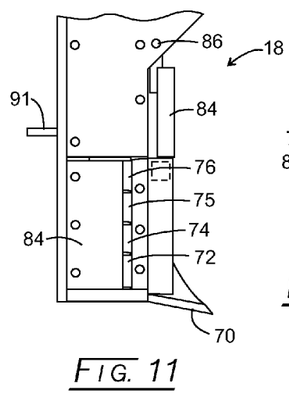
FIG. 11 is close up view of the knife assembly.
Figure 12:
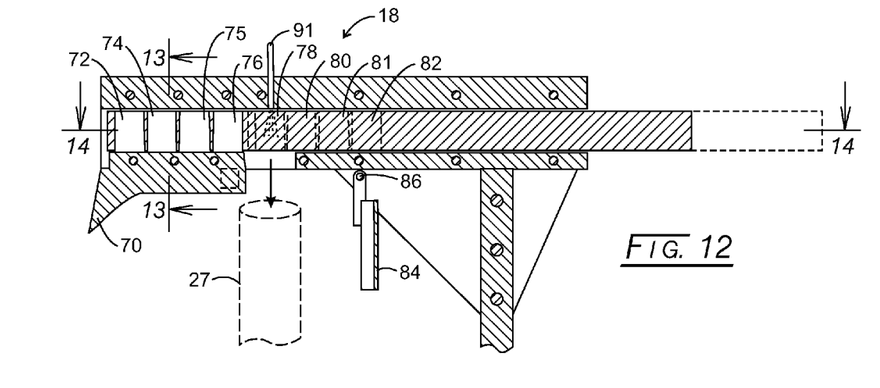
FIG. 12 is a sectional view taken along line 12-12 of FIG. 8.
Figure 13:
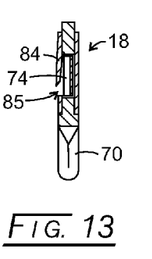
FIG. 13 is a sectional view taken along line 13-13 of FIG. 12.

Further detail on cup mover assembly 30 is revealed in FIG. 8. In particular, the opening, 64, below collection cup 50 is shown in phantom. A cam, 66, of cup cam assembly 30, is shown centrally disposed and which is rotated to take cup 50 and transfer the cup, 50, to the fill position. When cup 50 is urged out of cup mover assembly 30, is it pushes again the last filled cup, 50, and out onto table 52, the rearward portion of which defines a collection station 53 (as designated in FIGS. 3-7) where all filled collection cups are stored.

Figure 14:
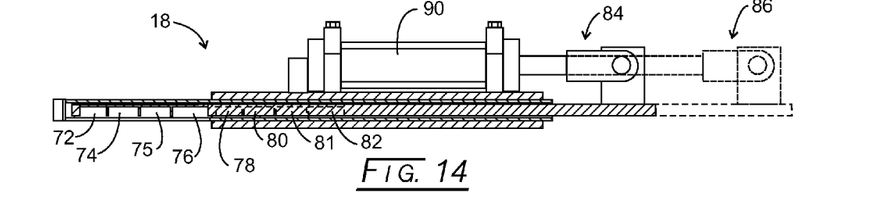
FIG. 14 is a sectional view taken along line 14-14 of FIG. 12.

FIGS. 9-12 show various aspects of collection knife assembly 18. When the knife blade is lowered 70, it actually cuts into the soil. There are 4 soil chambers housed within knife blade assembly 18. Each such chamber is revealed in FIG. 11, either empty, 72, 74, 75, and 76, or filled with soil, 78, 80, 81, and 82. A clean out guard, 84, (see also FIG. 12) actuates as the knife, 86, is raised to provide an opening to extract the filled soil chambers out of the knife. A cylinder assembly, 90, actuates the fore and aft movement of the chamber assembly, 85. See also FIG. 14 in this regard. An air nozzle, 91 (see FIG. 12) blows high-pressure air into the chambers to clean them.

While all of the chambers can be combined for producing a composite of the soil at various depths where the sample is taken is illustrated in the drawings, it also is possible to separately collect in collections cups soil housed within each chamber. That would provide a soil sample at various depths in a defined location where the samples are taken. It should be understood further that the depth of collection knife assembly 18 can be set by the operator to the limits of the equipment.

It should be understood that several of the limit switches necessary for determining the completion and/or return to home of several of the moving components described above have not been shown in position in order to not overly complicate the drawings and illustrative description set forth herein, but are to be provided as is necessary, desirable, or convenient in conventional fashion.

Figure 16:
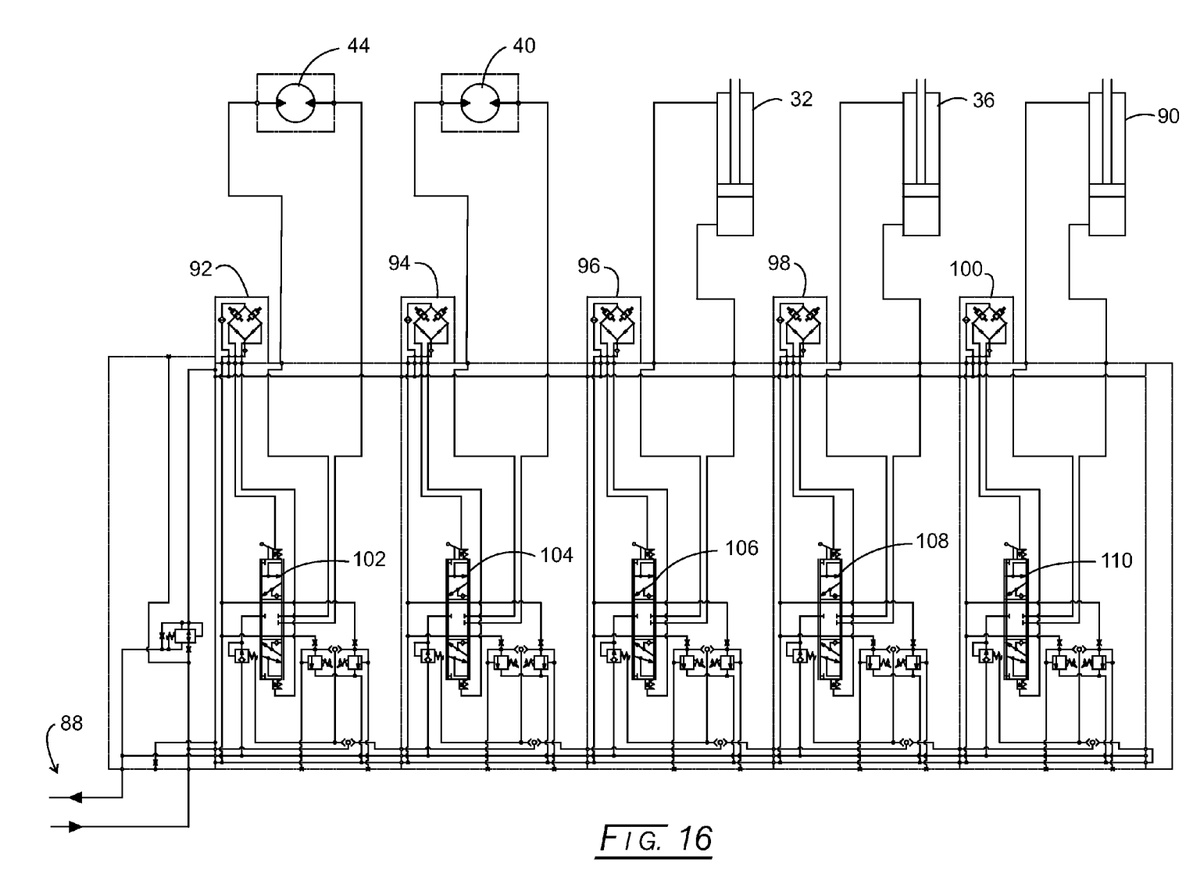
FIG. 16 is the hydraulic schematic for the soil sampler.

Referring now to FIG. 16, the generally hydraulic system is illustrated starting with the take off, 88, from tractor 10. Motors and hydraulic cylinders are labeled as they have been in the other figures. Solenoid valves, 92-100, are to be provided in conventional fashion, as are hydraulic valves, 102-110. The actual pluming of the hydraulic lines also is completed in conventional fashion.

In order to operative the soil sampling system whose components have been described above, the operator may use a Renu Controller, such as model FT4057T-E (Renu Electronics PVT Ltd, Batavia, Ill.). Such controller has 5 module slots. Slots 1 and 2 may have digital modules inserted, such as FIDD0808P having 8 digital input and output signals, while slots 3-5 can have analog modules inserted, such as FPRA0202L having 2 analog input and output signals. Such controller will be described in FIG. 15 for operation of the disclosed soil sampling system. It will be appreciated that other controllers could be used to advantage in accordance with the precepts disclosed herein.

Figure 16A:
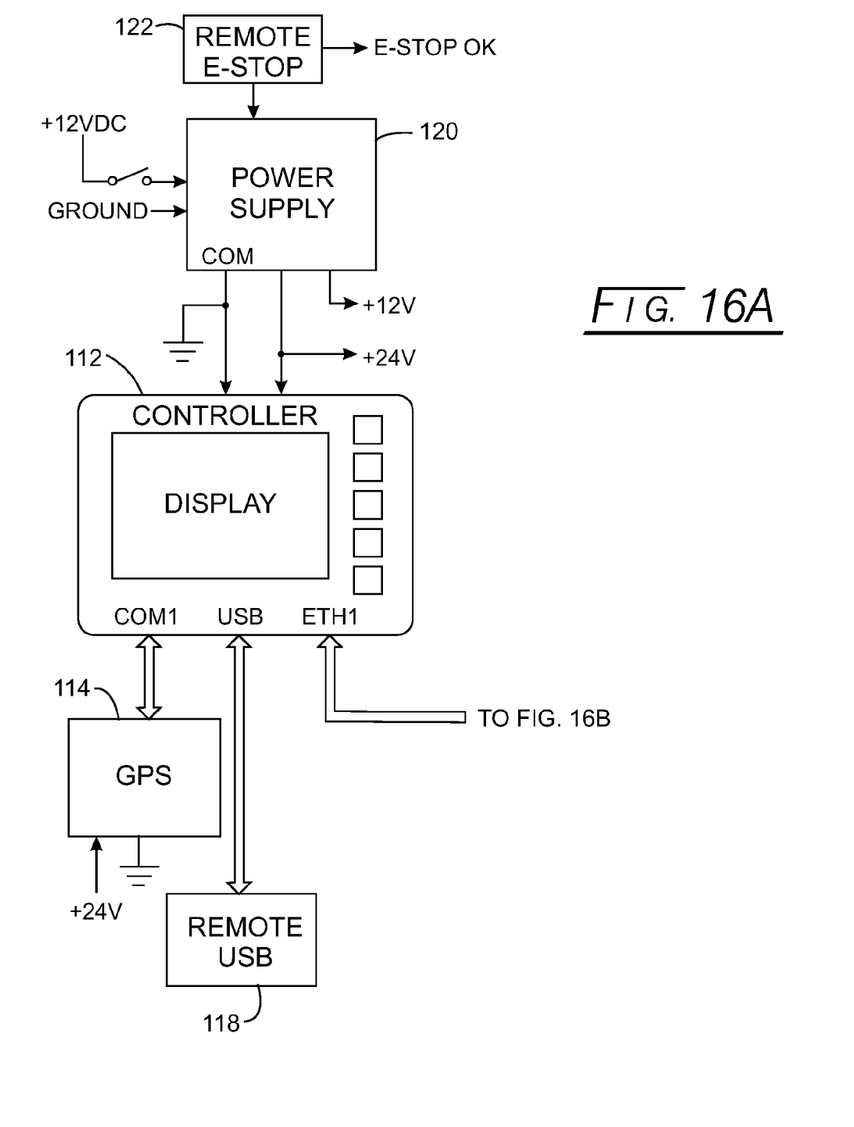
FIGS. 16A and 16B are the electrical block diagrams for the soil sampler; The drawings will be described is further detail below

Referring to FIG. 16A, a controller, 112, is the Renu controller identified above having 5 slots filled with the modules identified above. As described above, controller 112 as communication ports for GPS input, 114, and barcode reader, 116. Controller also has a USB port for a portable memory device, 118, for recordation of the data collected during a soil sampling run. Controller 112 also has a touchscreen display and a power supply, 120, input. Power supply 120 has an emergency stop, 122, and receives power from tractor 10 and outputs both a 12V signal and a 24V signal.

Figure 15A:
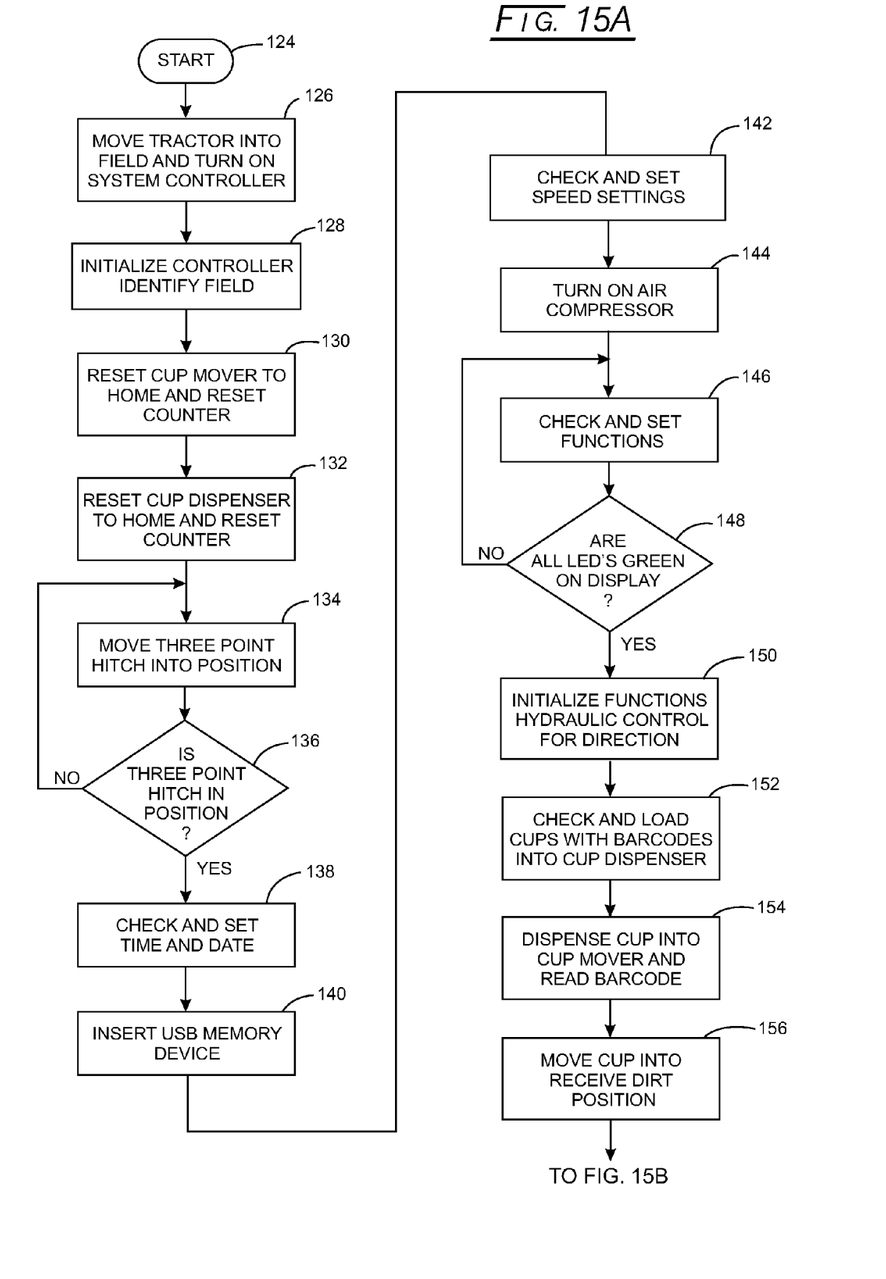
FIGS. 15A, 15B, and 15C are the flow chart for how the soil sampler operates.

Each of the 5 I/O slots are represented along with their function in the indicated boxes in FIG. 15 along with associated motors, relays, solenoids, hydraulic pistons, encoders, and the like. FIG. 16B will be described in connection with the flow sheets of FIGS. 15A-C. The method of collecting soil samples using the disclosed soil sampling system starts in box 124 by moving the tractor into the field and turning on controller 112, as represented in box 126, by turning on power supply 120. Controller 120 is initialized and the field to be sampled identified in box 128. In box 130, the cup mover is reset to home and the cup counter is reset. In box 132, the cup dispenser is reset to home along with its corresponding counter. Both of these actions are accomplished in I/O Slot 1 where encoder signals active a motor and hydraulic valve controlled by I/O slot 3.

The 3-point hitch of tractor 10 is moved into position in box 134, which is controller by I/P Slot 3. Decision box 136 is encountered which determines whether the 3-point hitch has fully moved into position. If not, steps 134 and 136 are repeated until the hitch is in position. At this point in box 138, the time and date are checked and/or entered into controller 112 and the operator reminded to insert portable memory device 118 into controller 112. In box 142 the tractor speed settings are checked and/or set and the high-pressure air (valves, cylinders, motors) turned on in box 144. In box 146, all controller functions are checked and/or set. Finally, in box 148 the operator polls the LED lights on controller 112 to see if they are all green. If not, the operation in box 146 is repeated until all green lights are seen.

The operation proceeds to box 150 where directions of the hydraulic cylinders are initialized. In box 152 the operator is reminder to load cups into the cup carousel 26 with the bar coded cups. A first cup is dispensed and its bar code read in box 154 and moved into position to receive dirt in box 156.

Figure 15B:
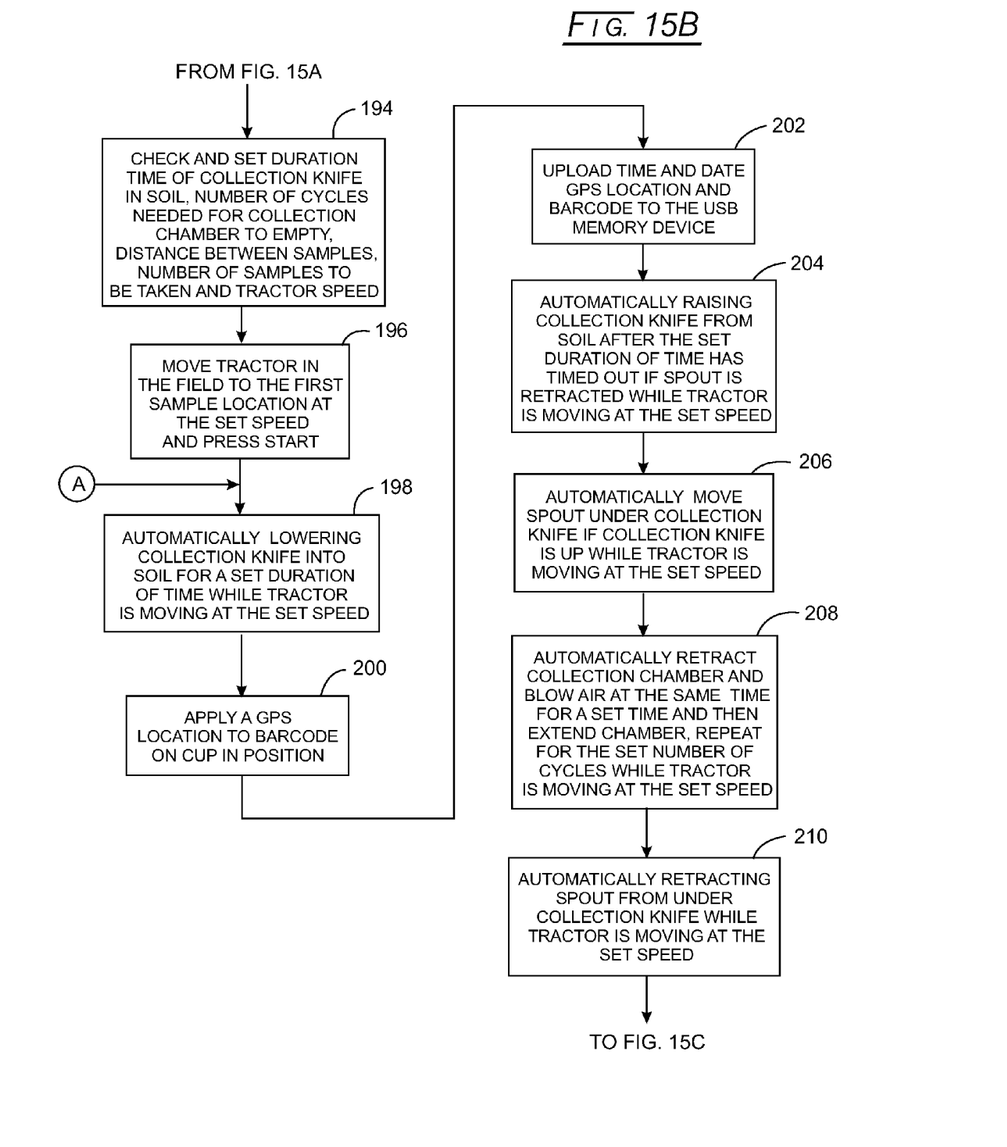
Figure 16B:
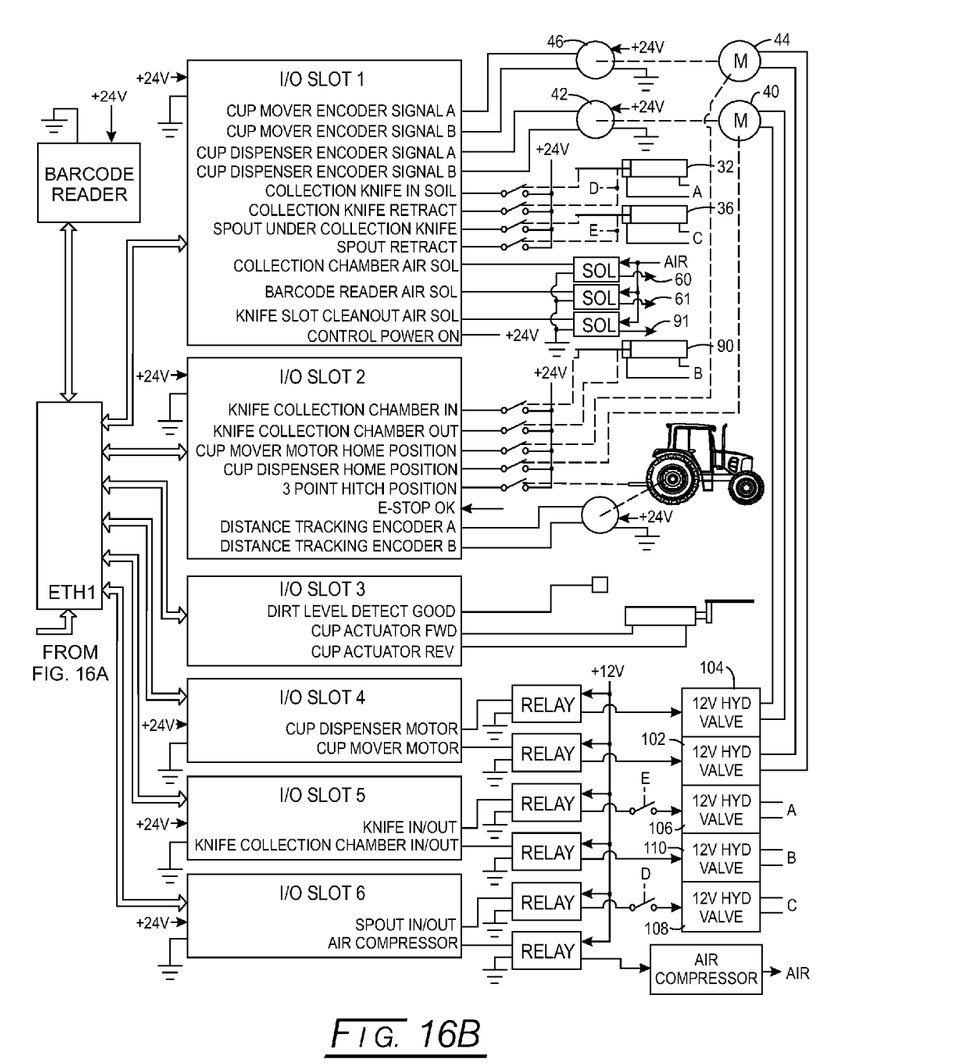

Continuing now with FIG. 15B, the process proceeds to box 194, where the operator checks and/or sets the time duration of soil sample collection (say, 7 sec.), the number of cycles needed for emptying the collection chambers (say, 3 cycles), and the distance between sample, and speed calibration (say, 5.0'/encoder click). In box 196, tractor 10 is moved into the field at the first collection location. In box 198, collection knife assembly 18 is automatically lowered for a pre-set time duration again while tractor 10 moves a set speed. In box 200, like the manual mode, the GPS location is correlated with the cup bar code and this data uploaded to memory device 118 in box 202. In box 204, collection knife assembly 18 is automatically raised after the set duration has timed out if transfer tube 27 is in a retracted position. In box 206, transfer tube 27 is automatically moved into a collection position, provided that collection knife assembly 18 is in a retracted position.

Figure 15C:
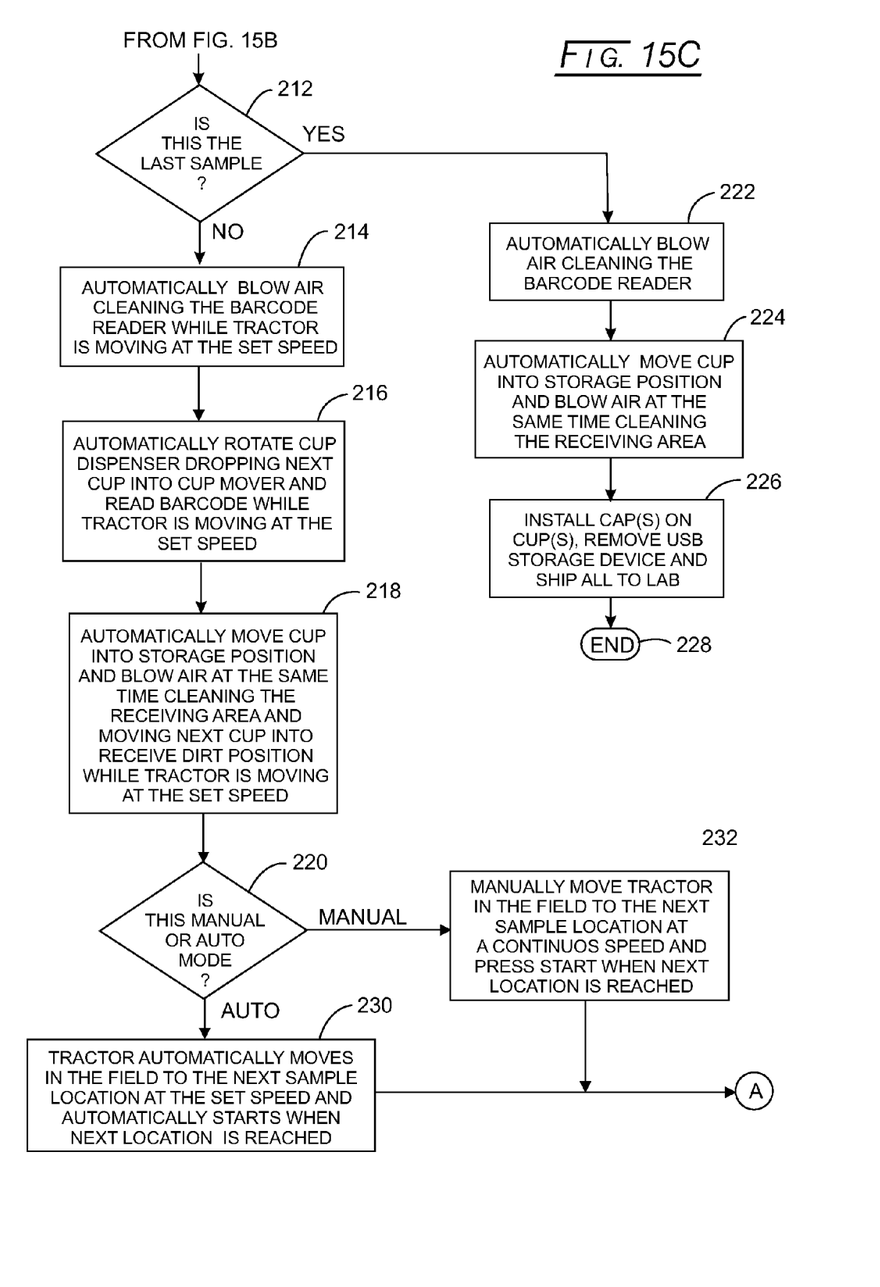

The collection chambers are retracted automatically and high-pressure air is blown across the chambers for a set time duration and this operation repeated a designated (say, 3) times in box 208. Transfer tube 27 is automatically retracted from under the chambers in box 210. Referring now to FIG. 15C and box 212, the question is posed whether this is the last sample, if not the process proceeds to box 214.

In box 214, air is automatically blown across the bar code reader to clean it. Cup carousel 26 is automatically rotated to the next position to drop a next cup down for its barcode to be read in box 216. The cup with the last sample is automatically moved onto floor 52 while air cleans the soil transfer area and the next dispensed cup is moved into position to receive a next soil sample in box 218. In box 220, the question is posed whether the sampler is in automatic or manual mode. If in automatic mode, the soil collection procedure proceeds to box 230 where the tractor is automatically moved in the field to the location of the next sample whereat the sample taking procedure automatically commences. At box 220 if the procedure is in manual mode, the procedure goes to box 232 where the tractor is manually driven at a continuous speed in the field to the next sample location. When the next sample location is reached, the operator presses 'start' at box 124 for the soil collection procedure to commence, as described above. Whether manual mode at box 224 or automatic mode at box 222, the procedure returns to location "A" between boxes 196 and 198 in FIG. 15B and the soil collection procedure is executed.

In box 212, if the last sample has been taken, the process proceeds to box 222 where the bar code reader is automatically cleaned with high-pressure air. In box 224, the last filled cup is automatically moved onto floor 52 and the transfer area where the last filled cup just came from cleaned with high-pressure air. In box 226, the operator must install caps on all cups, remove memory device 118, and ship everything back to a lab for analysis. End 228 has been reached.

While the soil sample and soil sampling system have been described with reference to various embodiments, those skilled in the art will understand that various changes may be made and equivalents may be substituted for elements thereof without departing from the scope and essence of the disclosure. In addition, many modifications may be made to the teachings of the disclosure in order to adapt to a particular situation or material without departing from the essential scope thereof. Therefore, it is intended that the disclosure not be limited to the particular embodiments disclosed, but that the disclosure will include all embodiments falling within the scope of the appended claims. In this application all units are in the US engineering system and all amounts and percentages are by weight, unless otherwise expressly indicated. Also, all citations referred herein are expressly incorporated herein by reference.

We claim:

1. A method for taking samples of topsoil, which comprises:
   (a) cutting a shallow furrow in the topsoil forward of a topsoil collection assembly and moving debris to the side;

(b) urging a sample of said topsoil into said topsoil collection assembly with a slanted rotating discus disposed opposite said topsoil collection assembly;
(c) moving an identified cup from a cup carrousel to a soil filling station;
(d) emptying said sample of topsoil into said identified cup;
(e) associating an identifier carried by said identified cup with a collection location of said sample of topsoil; and
(f) moving said identified cup into a collection station.

2. The method of claim 1, where a tractor towing said topsoil collection assembly includes a GPS unit and provides GPS data corresponding to said collection location.

3. The method of claim 1, wherein the topsoil is broken down by a soil breakdown assembly comprises a cutting rotating disk that cuts a shallow furrow in said topsoil followed by a pair of inwardly toed teethed disks that push debris to the side.

4. The method of claim 1, wherein the topsoil collection assembly comprises a sampling knife has a forward sharp leading edge behind which are a series of empty chambers into which topsoil to be collected is urged by forward movement through said topsoil and said oppositely disposed rotating discus.

5. The method of claim 1, including the step of:
using pressurized air to empty said sample of topsoil from said topsoil collection assembly.

6. The method of claim 1, wherein said identified cup is moved from said cup carrousel to said soil filling station by a cam assembly that rotates said identified cup below a tube to receive said sample of topspoil, whereafter said cam assembly rotates additionally to urge said identified cup out of said cam assembly and into said collection station.

7. The method of claim 6, wherein said rotating cam assembly is associated with an encoder for determining the location of the identified cup, a bar code reader for reading an information code on said cup below said tube receiving said sample of topspoil and sending said code and said collection location to memory for storage.

* * * * *